United States Patent [19]

Suarez et al.

[11] 4,400,543

[45] Aug. 23, 1983

[54] 3-PHENYL-4-BENZOYL-1,2-DIHYDRONAPHTHALENES

[75] Inventors: Tulio Suarez; C. David Jones, both of Indianapolis, Ind.

[73] Assignee: Eli Lilly and Company, Indianapolis, Ind.

[21] Appl. No.: 344,332

[22] Filed: Feb. 1, 1982

Related U.S. Application Data

[60] Division of Ser. No. 148,640, May 12, 1980, Pat. No. 4,323,707, which is a division of Ser. No. 930,639, Aug. 3, 1978, Pat. No. 4,230,862, which is a continuation of Ser. No. 761,930, Jan. 24, 1977, abandoned, which is a continuation-in-part of Ser. No. 724,202, Sep. 17, 1976, abandoned, which is a continuation-in-part of Ser. No. 625,991, Oct. 28, 1975, abandoned.

[51] Int. Cl.³ .............................................. C07C 49/82
[52] U.S. Cl. .................................................... 568/327
[58] Field of Search ...................................... 568/327

[56] References Cited

U.S. PATENT DOCUMENTS 4,017,546  4/1977  Suarez et al. ................. 568/327
4,323,707  4/1982  Suarez et al. ................. 564/324

*Primary Examiner*—Robert V. Hines
*Attorney, Agent, or Firm*—William C. Martens; Arthur R. Whale

[57] ABSTRACT

Derivatives of 3-phenyl-4-aroyl-1,2-dihydronaphthalenes and 1-aroyl-2-phenylnaphthalenes are useful as antifertility agents.

3 Claims, No Drawings

3-PHENYL-4-BENZOYL-1,2-DIHYDRONAPHTHALENES

CROSS REFERENCE

This application is a divisional of application Ser. No. 148,640, filed May 12, 1980, and now U.S. Pat. No. 4,323,707, which is a division of application Ser. No. 930,639, filed Aug. 3, 1978, now U.S. Pat. No. 4,230,862, which is a continuation of application Ser. No. 761,930, filed Jan. 24, 1977, now abandoned, which is a continuation-in-part of application Ser. No. 724,202, filed Sept. 17, 1976, now abandoned, which is a continuation-in-part of application Ser. No. 625,991, filed Oct. 28, 1975, now abandoned.

BACKGROUND OF THE INVENTION

This invention relates to novel compounds. More particularly, this invention relates to novel compounds which possess valuable utility as antifertility agents and thus are useful in the control of animal populations. In another aspect, this invention relates to a novel method of inhibiting pregnancy and to a novel method of controlling animal populations.

The prior art has recognized various classes of compounds, each having the general formula

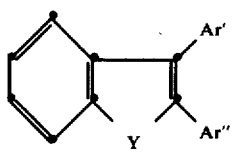

in which Ar is an aryl moiety and Y is any of various groups, such as —CH$_2$—, —CH$_2$—CH$_2$—, —S—, —NH—, —OCH$_2$, —O—, —CH$_2$S—, and —SCH$_2$—. Many compounds within these general classes are described as having antifertility activity.

Lednicer et al., *J. Med. Chem.*, 8, (1965), pp. 52–57, discloses 2,3-diphenylindenes and derivatives thereof as antifertility agents.

Lednicer et al., *J. Med. Chem.*, 9, (1966), pp. 172–175; Lednicer et al. *J. Med. Chem.*, 10, (1967), pp. 78–84; and Bencze et al., *J. Med. Chem.*, 8, (1965), pp. 213–214, each disclose various 1,2-diaryl-3,4-dihydronaphthalenes as active antifertility agents. In addition, U.S. Pat. Nos. 3,274,213; 3,313,853; 3,396,169; and 3,567,737 disclose various 1,2-diphenyl-3,4-dihydronaphthalenes as useful antifertility agents.

Other United States Patents disclose both 1,2-diphenyl-3,4-dihydronaphthalenes and 2,3-diphenylindenes as active agents. These include U.S. Pat. Nos. 3,293,263; 3,320,271; 3,483,293; 3,519,675; 3,804,851; and 3,862,232.

In addition, Crenshaw et al., *J. Med. Chem.*, 14, (1971), pp. 1185–1190, discloses, among others, various 2,3-diarylbenzothiophenes as exhibiting antifertility activity. Certain of these compounds are claimed in U.S. Pat. No. 3,413,305. Crenshaw et al. additionally disclose other compounds which participate in the general classes described hereinabove. 2,3-Diarylbenzofurans corresponding generally to the above benzothiophenes are disclosed and claimed in U.S. Pat. No. 3,394,125.

A need still exists to provide additional compounds useful as antifertility agents and, in particular, nonsteroidal antifertility agents. The novel compounds of this invention fill such a need. They are 3-phenyl-4-aroyl-1,2-dihydronaphthalenes and 1-aroyl-2-phenylnaphthalenes, and, structurally, they differ significantly from those described in the aforementioned prior art. It is an object therefore of this invention to provide novel nonsteroidal compounds having antifertility activity.

SUMMARY AND DETAILED DESCRIPTION OF THE INVENTION

These as well as other objects are achieved by this invention which comprises a class of compounds having the formula

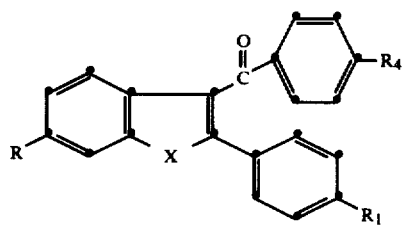

in which X is —CH$_2$—CH$_2$— or —CH=CH—; R is hydrogen, hydroxyl, or C$_1$–C$_5$ alkoxy; R$_1$ is hydrogen, hydroxyl, or C$_1$–C$_5$ alkoxy; R$_4$ is hydroxy or

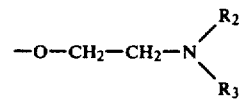

and R$_2$ and R$_3$ independently are C$_1$–C$_4$ alkyl, or R$_2$ and R$_3$ taken together with the nitrogen to which they are bonded constitute a heterocyclic ring selected from the group consisting of pyrrolidino, piperidino, hexamethyleneimino, or morpholino; and pharmaceutically acceptable non-toxic acid addition salts of those compounds in which R$_4$ is

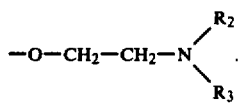

As indicated above, this invention also includes the defined compounds in which R$_4$ is

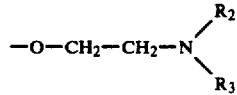

in the form of their pharmaceutically acceptable non-toxic acid addition salts. The pharmaceutically acceptable non-toxic acid addition salts include the organic and inorganic acid addition salts, for example, those prepared from acids such as hydrochloric, sulfuric, sulfonic, such as methanesulfonic, p-toluenesulfonic, β-naphthalenesulfonic, benzenesulfonic, and the like, tartaric, fumaric, hydrobromic, glycolic, citric, maleic, phosphoric, succinic, acetic, nitric, and the like. Preferably, the acid addition salts are those prepared from citric acid or from sulfonic acids, such as methanesulfonic (mesylate), p-toluenesulfonic (tosylate), and β-naphthalenesulfonic (β-napsylate). Most preferred salts include the mesylates, tosylates, and β-napsylates. Such salts are prepared by conventional methods.

The term "$C_1$-$C_4$ alkyl" as used herein contemplates both straight and branched chain groups such as methyl, ethyl, n-propyl, isopropyl, n-butyl, t-butyl, isobutyl, and sec-butyl.

The term "$C_1$-$C_5$ alkoxy" as used herein contemplates both straight and branched chain alkyl radicals and therefore defines groups such as, for example, methoxy, ethoxy, n-propoxy, isopropoxy, n-butyloxy, isobutyloxy, t-butyloxy, sec-butyloxy, n-amyloxy, isoamyloxy, t-amyloxy, sec-amyloxy, and the like. Of the $C_1$-$C_5$ alkoxy groups defined herein, methoxy is highly preferred.

Those compounds of this invention in which $R_4$ is hydroxyl are useful as intermediates in the preparation of those compounds of this invention which are active as antifertility agents.

A preferred subclass of the compounds of this invention are the dihydronaphthalenes, having a basic side chain that is, in the above formula, those compounds in which X is —$CH_2$—$CH_2$— and $R_4$ is

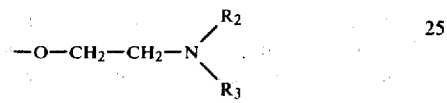

Of the defined dihydronaphthalenes, several preferred subclasses exist. One such subclass is comprised of 7-alkoxy-1,2-dihydronaphthalenes, that is, those compounds in which X is —$CH_2$—$CH_2$— and R is $C_1$-$C_5$ alkoxy.

Another subclass includes the non-hydroxylated or alkoxylated dihydronaphthalenes, that is, those compounds in which X is —$CH_2$—$CH_2$— and both R and $R_1$ are hydrogen.

A further preferred subclass includes 3-(4'-alkoxyphenyl)-7-alkoxy-1,2-dihydronaphthalenes, that is, those compounds in which X is —$CH_2$—$CH_2$— and both R and $R_1$ are $C_1$-$C_5$ alkoxy.

Further preferred subclasses include 3-(4'-hydroxyphenyl)-1,2-dihydronaphthalenes and 7-hydroxy-1,2-dihydronaphthalenes, that is, those compounds in which X is —$CH_2$—$CH_2$— and R or $R_1$ is hydroxy.

Another preferred subclass comprises 3-(4'-hydroxyphenyl)-7-hydroxy-1,2-dihydronaphthalenes, that is, those compounds in which X is —$CH_2$—$CH_2$— and both R and $R_1$ are hydroxy.

A most preferred subclass comprises 3-(4'-alkoxyphenyl)-1,2-dihydronaphthalenes, that is those compounds in which X is —$CH_2$—$CH_2$—, R is hydrogen, and $R_1$ is $C_1$-$C_5$ alkoxy.

Another preferred subclass includes those compounds of this invention in which $R_4$ is

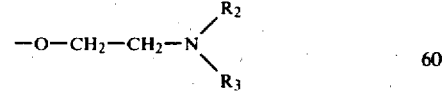

and both $R_2$ and $R_3$ are methyl, both $R_2$ and $R_3$ are ethyl, or $R_2$ and $R_3$ taken together with the nitrogen to which they are bonded constitute a pyrrolidino or a piperidino ring.

The compounds of this invention are prepared by the following sequences, the dihydronaphthalene structures in general being precursors to the naphthalene compounds.

A. Preparation of Compounds in which X is —$CH_2$—$CH_2$—

A tetralone of the formula

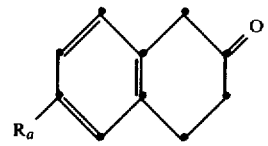

in which $R_a$ is hydrogen, $C_1$-$C_5$ alkoxy, or benzyloxy, is reacted with a phenyl benzoate of the formula

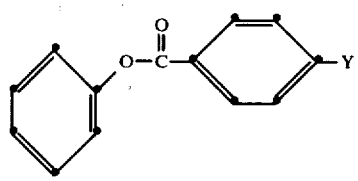

in which Y is methoxy, benzyloxy, or

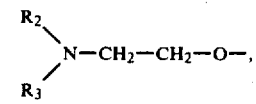

$R_2$ and $R_3$ being as aforedefined.

The reaction generally is carried out in the presence of a moderately strong base such as sodium amide and at room temperature or below.

The product which is obtained is a substituted tetralone of the formula

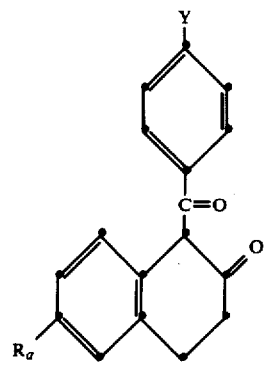

The substituted tetralone (III) then is reacted under Grignard reaction conditions with the Grignard reagent of the formula

in which $R_{1a}$ is hydrogen, $C_1$-$C_5$ alkoxy, or benzyloxy.

The compound which is produced, a 3-phenyl-4-aroyl-1,2-dihydronaphthalene, has the formula

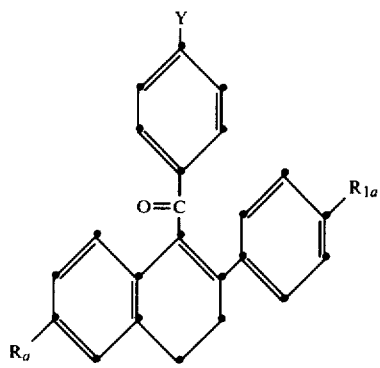

and, depending upon the identity of the groups $R_a$, $R_{1a}$, and Y, may be a compound of this invention.

In these instances in which Y is methoxy, the compound (V) can be treated with pyridine hydrochloride at reflux to produce the corresponding hydroxy compound. Under these conditions, should $R_a$ and/or $R_{1a}$ be alkoxy or benzyloxy, these groups also will be cleaved to hydroxyl groups.

In those instances in which Y in compound (V) is methoxy or benzyloxy, and $R_a$ and/or $R_{1a}$ are alkoxy or benzyloxy, the group at Y can be selectively cleaved by treating the compound with an equivalent of sodium thioethoxide in N,N-dimethylformamide at a moderately elevated temperature of about 80° C. to about 90° C. The ongoing of the selective cleavage can be monitored by periodic thin-layer chromatographic analysis (TLC) of the reaction mixture. The reaction is complete when little or no starting material remains.

Once the aforedescribed compound in which Y has been converted to hydroxyl is generated, it can be treated with a compound of the formula

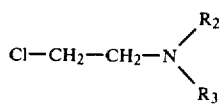

in which $R_2$ and $R_3$ are as aforedescribed, to produce a compound of this invention. Under the usual reaction conditions, of course, alkylation will be effected at each of the hydroxyl groups which may be present in the molecule. This, however, can be avoided, and alkylation at the 4-benzoyl group alone can be achieved by carrying out the reaction in the presence of an excess of finely powdered potassium carbonate and using an equivalent or a slight excess of the 1-chloro-2-aminoethane compound.

Depending upon the intended structure of the final product, the compound containing the 2-aminoethoxy substituent they can be further treated with an additional quantity of sodium thioethoxide in N,N-dimethylformamide as aforedescribed to effect cleavage of any remaining alkoxy or benzyloxy groups, thereby providing another sequence for achieving formation of those compounds of this invention in which R and/or $R_1$ are hydroxyl.

In any of the above, it is evident that the particular sequence of synthetic steps designed to produce a compound having substituents of particular definition and location is such as one of ordinary skill in the art will well recognize.

B. Preparation of Compounds in which X is —CH=CH—

These compounds are readily prepared from the aforementioned compounds in which X is —CH$_2$—CH$_2$—. Selective dehydrogenation of the dihydronaphthalene structure to produce specifically the corresponding naphthalene can be accomplished by treatment of the former with 2,3-dichloro-5,6-dicyano-1,4-benzoquinone (DDQ) at a temperature of from about 50° C. to about 100° C.

Again, by means of the aforementioned derivatizing reactions, the naphthalene which is produced can be converted to other naphthalene compounds within the scope of this invention.

The compounds of this invention are valuable pharmaceutical agents. They exhibit anti-fertility activity, and they especially are useful as orally active anti-fertility agents in birds and mammals. The compounds of this invention thus are useful in controlling the animal population and as contraceptives in living beings. The compounds of this invention also are valuable for animal pest control. For example, the compounds of this invention can be formulated in combination with baits and/or attractants and placed in feeding stations accessible to undesirable rodents and other small animals including Canidae such as coyotes, foxes, wolves, jackals, and wild dogs, and birds, such as starlings, galls, redwing blackbirds, pigeons, and the like, to greatly reduce the population thereof. By reason of the activity of the compounds of this invention, they can be used to reduce hazards to aviation by lessening the presence of birds and animals on runways and in the vicinity of air fields. The compounds of this invention also can be used to reduce the population of undesirable birds and animals so as to aid in the prevention and the spread of disease, and to reduce the destruction of property in both rural and urban areas.

The compounds of this invention can be administered as such, or they can be compounded and formulated into pharmaceutical preparations in unit dosage form for oral or parenteral administration. In the compounding or formulation, organic or inorganic solids and/or liquids which are pharmaceutically acceptable carriers can be employed. Suitable such carriers will be well recognized by those of ordinary skill in the art. The compositions may take the form of tablets, powder granules, capsules, suspensions, solutions, and the like.

The compounds of this invention, when administered in an effective amount, will produce the inhibition of pregnancy in mammals. The usual daily dose is from about 0.02 milligrams to about 20 milligrams per kilogram body weight of the recipient. The preferred anti-fertility daily dose is from about 0.02 milligrams to about 0.4 milligrams per kilogram body weight of the recipient.

Examples of compounds of this invention include the following:

3-(4-hydroxyphenyl)-4-[4-(2-pyrrolidinoethoxy)benzoyl]-1,2-dihydronaphthalene;

3-(4-methoxyphenyl)-4-[4-(2-diethylaminoethoxy)benzoyl]-1,2-dihydronaphthalene;

3-(4-isopropoxyphenyl)-4-[4-(2-pyrrolidinoethoxy)benzoyl]-1,2-dihydronaphthalene;

3-(4-t-butyloxyphenyl)-4-[4-(2-hexamethyleneiminoethoxy)benzoyl]-1,2-dihydronaphthalene;

3-(4-pentyloxyphenyl)-4-[4-(2-morpholinoethoxy)benzoyl]-1,2-dihydronaphthalene;

3-(4-methoxyphenyl)-4-[4-(2-piperidinoethoxy)benzoyl]-1,2-dihydronaphthalene;
3-(4-ethoxyphenyl)-4-[4-(2-dimethylaminoethoxy)benzoyl]-1,2-dihydronaphthalene;
3-(4-n-propoxyphenyl)-4-[4-(2-pyrrolidinoethoxy)benzoyl]-1,2-dihydronaphthalene;
3-(4-sec-butyloxyphenyl)-4-[4-(2-piperidinoethoxy)benzoyl]-1,2-dihydronaphthalene;
3-(4-ethoxyphenyl)-4-[4-(2-morpholinoethoxy)benzoyl]-1,2-dihydronaphthalene;
3-(4-hydroxyphenyl)-4-[4-(2-hexamethyleneiminoethoxy)benzoyl]-1,2-dihydronaphthalene;
3-(4-methoxyphenyl)-4-[4-(2-dimethylaminoethoxy)benzoyl]-1,2-dihydronaphthalene;
3-(4-isopropoxyphenyl)-4-[4-(2-diethylaminoethoxy)benzoyl]-1,2-dihydronaphthalene;
3-(4-t-butyloxyphenyl)-4-[4-(2-pyrrolidinoethoxy)benzoyl]-1,2-dihydronaphthalene;
3-(4pentyloxyphenyl)-4-[4-(2-piperidinoethoxy)benzoyl]-1,2-dihydronaphthalene;
3-(4-isobutyloxyphenyl)-4-[4-(2-morpholinoethoxy)benzoyl]-1,2-dihydronaphthalene;
3-(4ethoxyphenyl)-4-[4-(2-pyrrolidinoethoxy)benzoyl]-1,2-dihydronaphthalene;
3-(4-n-propyloxyphenyl)-4-[4-(2-dimethylaminoethoxy)-benzoyl]-1,2-dihydronaphthalene;
3-(4-hydroxyphenyl)-4-[4-(2-diethylaminoethoxy)benzoyl]-1,2-dihydronaphthalene;
3-(4-methoxyphenyl)-4-[4-(2-pyrrolidinoethoxy)benzoyl]-1,2-dihydronaphthalene;
3-(4-hydroxyphenyl)-4-[4-(2-piperidinoethoxy)benzoyl]-1,2-dihydronaphthalene;
3-(4-hydroxyphenyl)-4-[4-(2-morpholinoethoxy)benzoyl]-1,2-dihydronaphthalene;
3-(4-hydroxyphenyl)-4-[4-(2-dimethylaminoethoxy)benzoyl]-7-hydroxy-1,2-dihydronaphthalene;
3-(4-methoxyphenyl)-4-[4-(2-diethylaminoethoxy)benzoyl]-7-methoxy-1,2-dihydronaphthalene;
3-(4-isopropoxyphenyl)-4-[4-(2-pyrrolidinoethoxy)benzoyl]-7-ethoxy-1,2-dihydronaphthalene;
3-(4-t-butyloxyphenyl)-4-[4-(2-dimethylaminoethoxy)benzoyl]-7-propoxy-1,2-dihydronaphthalene;
3-(4-pentyloxyphenyl)-4-[4-(2-piperidinoethoxy)benzoyl]-7-pentyloxy-1,2-dihydronaphthalene;
3-(4-hydroxyphenyl)-4-[4-(2-pyrrolidinoethoxy)benzoyl]-7-hydroxy-1,2-dihydronaphthalene;
3-(4-ethoxyphenyl)-4-[4-(2-morpholinoethoxy)benzoyl]-7-ethoxy-1,2-dihydronaphthalene;
3-phenyl-4-[4-(2-dimethylaminoethoxy)benzoyl]-1,2-dihydronaphthalene;
3-phenyl-4-[4-(2-pyrrolidinoethoxy)benzoyl]-7-methoxy-1,2-dihydronaphthalene;
3-phenyl-4-[4-(2-dimethylaminoethoxy)benzoyl]-7-hydroxy-1,2-dihydronaphthalene;
3-phenyl-4-[4-(2-hexamethyleneiminoethoxy)benzoyl]-7-methoxy-1,2-dihydronaphthalene;
3-phenyl-4-[4-(2-pyrrolidinoethoxy)benzoyl]-7-hydroxy-1,2-dihydronaphthalene;
3-phenyl-4-[4-(2-piperidinoethoxy)benzoyl]-7-ethoxy-1,2-dihydronaphthalene;
3-phenyl-4-[4-(2-morpholinoethoxy)benzoyl]-7-methoxy-1,2-dihydronaphthalene;
3-phenyl-4-[4-(2-hexamethyleneiminoethoxy)benzoyl]-7-isopropoxy-1,2-dihydronaphthalene;
3-phenyl-4-[4-(2-dimethylaminoethoxy)benzoyl]-7-pentyloxy-1,2-dihydronaphthalene;
3-phenyl-4-[4-(2-pyrrolidinoethoxy)benzoyl]-7-ethoxy-1,2-dihydronaphthalene;
3-phenyl-4-[4-(2-morpholinoethoxy)benzoyl]-7-isopropoxy-1,2-dihydronaphthalene;
3-phenyl-4-[4-(2-hexamethyleneiminoethoxy)benzoyl]-7-butyloxy-1,2-dihydronaphthalene;
3-phenyl-4-[4-(2-diethylaminoethoxy)benzoyl]-7-hydroxy-1,2-dihydronaphthalene;
1-[4-(2-pyrrolidinoethoxy)benzoyl]-2-(4-hydroxyphenyl)naphthalene;
1-[4-(2-pyrrolidinoethoxy)benzoyl]-2-(4-n-propoxyphenyl)naphthalene;
1-[4-(2-piperidinoethoxy)benzoyl]-2-(4-sec-butyloxyphenyl)naphthalene;
1-[4-(2-diethylaminoethoxy)benzoyl]-2-(4-methoxyphenyl)naphthalene;
1-[4-(2-pyrrolidinoethoxy)benzoyl]-2-(4-isopropoxyphenyl)naphthalene;
1-[4-(2-hexamethyleneiminoethoxy)benzoyl]-2-(4-t-butyloxyphenyl)naphthalene;
1-[4-(2-morpholinoethoxy)benzoyl]-2-(4-pentyloxyphenyl)naphthalene;
1-[4-(2-piperidinoethoxy)benzoyl]-2-(4-methoxyphenyl)naphthalene;
1-[4-(2-dimethylaminoethoxy)benzoyl]-2-(4-ethoxyphenyl)naphthalene;
1-[4-(2-morpholinoethoxy)benzoyl]-2-(4-ethoxyphenyl)naphthalene;
1-[4-(2-hexamethyleneiminoethoxy)benzoyl]-2-(4-hydroxyphenyl)naphthalene;
1-[4-(2-dimethylaminoethoxy)benzoyl]-2-(4-methoxyphenyl)naphthalene;
1-[4-(2-diethylaminoethoxy)benzoyl]-2-(4-isopropoxyphenyl)naphthalene;
1-[4-(2-pyrrolidinoethoxy)benzoyl]-2-(4-t-butyloxyphenyl)naphthalene;
1-[4-(2-piperidinoethoxy)benzoyl]-2-(4-pentyloxyphenyl)naphthalene;
1-[4-(2-morpholinoethoxy)benzoyl]-2-(4-isobutyloxyphenyl)naphthalene;
1-[4-(2-pyrrolidinoethoxy)benzoyl]-2-(4-ethoxyphenyl)naphthalene;
1-[4-(2-dimethylaminoethoxy)benzoyl]-2-(4-n-propoxyphenyl)naphthalene;
1-[4-(2-diethylaminoethoxy)benzoyl]-2-(4-hydroxyphenyl)naphthalene;
1-[4-(2-pyrrolidinoethoxy)benzoyl]-2-(4-methoxyphenyl)naphthalene;
1-[4-(2-piperidinoethoxy)benzoyl]-2-(4-hydroxyphenyl)naphthalene;
1-[4-(2-morpholinoethoxy)benzoyl]-2-(4-hydroxyphenyl)naphthalene;
1-[4-(2-dimethylaminoethoxy)benzoyl]-2-(4-hydroxyphenyl)-6-hydroxynaphthalene;
1-[4-(2-diethylaminoethoxy)benzoyl]-2-(4-methoxyphenyl)-6-methoxynaphthalene;
1-[4-(2-pyrrolidinoethoxy)benzoyl]-2-(4-isopropoxyphenyl)-6-ethoxynaphthalene;
1-[4-(2-dimethylaminoethoxy)benzoyl]-2-(4-t-butyloxyphenyl)-6-propoxynaphthalene;
1-[4-(2-piperidinoethoxy)benzoyl]-2-(4-pentyloxyphenyl)-6-pentyloxynaphthalene;
1-[4-(2-pyrrolidinoethoxy)benzoyl]-2-(4-hydroxyphenyl)-6-hydroxynaphthalene;
1-[4-(2-morpholinoethoxy)benzoyl]-2-(4-ethoxyphenyl)-6-ethoxynaphthalene;
1-[4-(2-pyrrolidinoethoxy)benzoyl]-2-phenyl-6-methoxynaphthalene;
1-[4-(2-dimethylaminoethoxy)benzoyl]-2-phenyl-6-hydroxynaphthalene;

1-[4-(2-hexamethyleneiminoethoxy)benzoyl]-2-phenyl-6-methoxynaphthalene;

1-[4-(2-pyrrolidinoethoxy)benzoyl]-2-phenyl-6-hydroxynaphthalene;

1-[4-(2-piperidinoethoxy)benzoyl]-2-phenyl-6-ethoxynaphthalene;

1-[4-(2-morpholinoethoxy)benzoyl]-2-phenyl-6-methoxynaphthalene;

1-[4-(2-hexamethyleneiminoethoxy)benzoyl]-2-phenyl-6-isopropoxynaphthalene;

1-[4-(2-dimethylaminoethoxy)benzoyl]-2-phenyl-6-pentyloxynaphthalene;

1-[4-(2-pyrrolidinoethoxy)benzoyl]-2-phenyl-6-ethoxynaphthalene;

1-[4-(2-morpholinoethoxy)benzoyl]-2-phenyl-6-isopropoxynaphthalene;

1-[4-(2-hexamethyleneiminoethoxy)benzoyl]-2-phenyl-6-butyloxynaphthalene;

1-[4-(2-diethylaminoethoxy)benzoyl]-2-phenyl-6-hydroxynaphthalene;

and the like.

The following examples are illustrative of the preparation and activities of the compounds of this invention. They are not intended to be limiting upon the scope thereof.

EXAMPLE 1

Preparation of the Citrate Salt of 3-(4-methoxyphenyl)-4-[4-(2-pyrrolidinoethoxy)benzoyl]-1,2-dihydronaphthalene To a suspension of 15.2 grams (0.38 mole) of sodium amide in 250 ml. of tetrahydrofuran (THF) were added 50 grams (0.34 mole) of β-tetralone. The mixture was stirred for 15–20 minutes, and 78 grams of phenyl p-methoxybenzoate dissolved in THF were added. The temperature was maintained below 10° C., and the mixture then was stirred at room temperature overnight. The reaction mixture was concentrated, and water was added to the residue. The aqueous mixture was extracted with ethyl acetate, and the ethyl acetate extract was washed and concentrated. The residue was chromatographed on silica using benzene as eluant. The purer fractions obtained by the chromatographic separation were combined and concentrated, and the residue was dissolved in a minimum of methanol. The methanol was cooled, and 35.2 grams of 1-(p-methoxybenzoyl)-2-tetralone were collected by filtration, melting point 88°–91° C.

Analysis, Calcd. for $C_{18}H_{16}O_3$: C, 77.12; H, 5.75; O, 17.12. Found: C, 77.08; H, 5.54; O, 17.32.

Mass spectrum: Theory, 280; Found, 280.

p-Bromoanisole (18.7 grams; 0.1 mole) was added dropwise in ether to THF containing 5 drops of 1,2-dibromoethane and 3.6 grams (0.15 mole) of magnesium. Reaction occurred almost immediately, and the addition was continued at a slow rate with evolution of heat sufficient to maintain a general reflux. Upon completion of the addition, the above substituted β-tetralone dissolved in acetone was added dropwise with stirring over a two-hour period, the mixture being maintained at 40° C. The resulting mixture then was poured into cold, dilute hydrochloric acid, and the acidic mixture was extracted with ethyl acetate. The ethyl acetate extract was washed, dried, and concentrated to an oil. The oil was chromatographed over silica using benzene as eluant. Starting material (8.6 grams) was obtained as greenish-yellow crystals, melting point 86°–88° C., and 15 grams of 3-(4-methoxyphenyl)-4-(4-methoxybenzoyl)-1,2-dihydronaphthalene were obtained as an oil elution of the column with a mixture of benzene containing 2 percent ethyl acetate.

Analysis, Calcd. for $C_{25}H_{22}O_3$: C, 81.06; H, 5.99; O, 12.96. Found: C, 81.32; H, 6.13; O, 13.04.

A mixture of 11.1 grams (0.03 mole) of the above dimethoxy product, 7.2 grams of sodium hydride (50 percent in oil), and 11 ml. of ethyl mercaptan in N,N-dimethylformamide was prepared. The mixture was heated to 65°–70° C. for two hours. The mixture then was cooled and concentrated. The concentrate was acidified and extracted with ethyl acetate. The ethyl acetate extract was washed, dried, and evaporated. The residue was dissolved in benzene and chromatographed over silica to obtain five grams of an oil comprising relatively pure 3-(4-methoxyphenyl)-4-(4-hydroxybenzoyl)-1,2-dihydronaphthalene.

Analysis, Calcd. for $C_{24}H_{20}O_3$: C, 80.88; H, 5.66; O, 13.47. Found: C, 79.66; H, 5.87; O, 13.57.

The above phenolic product (4.3 grams; 0.01 mole) was dissolved in N,N-dimethylformamide. To this solution was added 0.7 gram of sodium hydride (50 percent in oil), and the resulting mixture was warmed to 40° C. for one hour and then was cooled to room temperature. To the mixture then were added 1.62 grams of 1-chloro-2-pyrrolidinoethane, and the mixture was warmed to 60° C. for two hours and then was stirred at room temperature overnight. The mixture was concentrated, and water was added to the residue. The aqueous mixture was extracted with ethyl acetate. The ethyl acetate extract was washed and concentrated to a residue. The residue was extracted with hexane, the insoluble portion was dissolved in ethyl acetate, and the ethyl acetate solution was extracted with 1 N hydrochloric acid. The acid extract was rendered alkaline, and then was extracted with ethyl acetate. The ethyl acetate extract was washed and concentrated. One equivalent of citric acid in acetone then was added to the concentrate, and the mixture was concentrated to dryness. The residue was dissolved in a large volume of methyl ethyl ketone. The ketone solution was concentrated to about 300 ml. and was cooled to 0° C. The product, the citrate salt of 3-(4-methoxyphenyl)-4-[4-(2-pyrrolidinoethoxy)benzoyl]-1,2-dihydronaphthalene, was collected by filtration and a vacuum dried, melting point 82°–85° C.

Analysis, Calcd. for $C_{36}H_{39}NO_{10}$: C, 66.96; H, 6.09; N, 2.17; O, 24.78. Found: C, 66.70; H, 6.27; N, 2.27; O, 24.54.

EXAMPLE 2

Preparation of the Citrate Salt of 3-Phenyl-4-[4-(2-pyrrolidinoethoxy)benzoyl]-7-methoxy-1,2-dihydronaphthalene To 300 ml. of DMF were added 107 grams of phenyl p-hydroxybenzoate and 26 grams of sodium hydride (50 percent in oil). The mixture was heated at 60° C. for two hours. To the mixture then were added 67 grams of 1-chloro-2-pyrrolidinoethane, and the mixture was stirred overnight at 85° C. The bulk of the DMF then was evaporated from the mixture. Water was added to the residue, and the aqueous mixture was extracted with ethyl acetate. The ethyl acetate extract was concentrated, and the residue was dissolved in a 1:1 mixture of ether and ethyl acetate. The organic solution then was extracted with 2 N hydrochloric acid, and the acid extract was added dropwise to 2 N sodium hydroxide. The resulting mixture was extracted with ethyl acetate, and the ethyl acetate extract was washed and then dried over magnesium sulfate. The ethyl acetate was concentrated to obtain 110 grams of crude phenyl p-(2-pyrrolidinoethoxy)benzoate.

To a suspension of 20 grams (0.5 mole) of sodium amide in tetrahydrofuran were added dropwise 41.7 grams of 6-methoxy-2-tetralone in THF, the temperature of the mixture being maintained below 10° C. Upon completion of the addition, the mixture was stirred for 20 minutes at below 10° C. after which time an exothermic reaction occurred, the temperature rising to about 20° C. The above-prepared phenyl p-(2-pyrrolidinoethoxy)benzoate dissolved in THF then was added dropwise, and the mixture was stirred at room temperature overnight. The mixture was poured into water, and the resulting mixture was extracted with ethyl acetate. The ethyl acetate extract was washed several times with water and dried over magnesium sulfate. The ethyl acetate then was concentrated to obtain about 100 grams of crude material which was dissolved in 1.5 liters of acetone, and one equivalent of citric acid in 400 ml. of ethyl acetate was added. The resulting solid was isolated by filtration and vacuum dried to obtain 85.9 grams of product, melting point 84° C., which proved to be 6-methoxy-1-[4-(2-pyrrolidinoethoxy)benzoyl]-2-tetralone and not the corresponding citric acid salt. The product then was chromatographed over silica using ethyl acetate as eluant, and the citrate salt was prepared from the recovered product.

Analysis, Calcd. for $C_{30}H_{35}NO_{11}$: C, 61.53; H, 6.02; N, 2.39; Found: C, 61.39; H, 5.78; N, 2.25.

The above product (8.6 grams; 0.02 mole) was added to a solution of phenylmagnesium bromide in THF. The resulting mixture was stirred for one hour at room temperature and then was warmed to 50° C. for three hours. The resulting mixture was poured into a mixture of ice and hydrochloric acid, and the acid mixture was extracted with ethyl acetate. The ethyl acetate extract was washed, dried, and concentrated to obtain 10.5 grams of a red-brown oil. The oil was added to 500 ml. of acetic acid, and the mixture was heated on a steam bath for about 30 minutes. The acid was stippred off, and water was added to the residue. The aqueous mixture was rendered alkaline by addition of base, and the alkaline mixture was extracted with ethyl acetate. The extract was dried and concentrated to obtain 8.7 grams of product which were dissolved in acetone, and one equivalent of citric acid was added to the mixture. The acetone was stripped off, and methyl ethyl ketone was added to the residue. The mixture was maintained at 0° C. overnight, and the crystals which formed were collected by filtration and washed with cold methyl ethyl ketone and vacuum dried, melting point 95°–100° C. The solid was recrystallized from acetone to obtain the title compound in the form of its citrate salt, melting point 98°–100° C.

Analysis, Calcd. for $C_{36}H_{39}NO_{10}$: C, 66.96; H, 6.09; N, 2.17; O, 24.78. Found: C, 66.72; H, 6.27; N, 2.09; O, 24.50.

The title compound in the form of its free base was generated by treatment of the citrate salt with dilute alkali.

Analysis, Calcd. for $C_{30}H_{31}NO_5$: C, 79.44; H, 6.89; N, 3.09; Found: C, 79.19; H, 6.68; N, 2.91.

EXAMPLE 3

Preparation of the Citrate Salt of 3-Phenyl-4-[4-(2-pyrrolidinoethoxy)benzoyl]-1,2-dihydronaphthalene To a solution of 5.0 grams (0.018 mole) of 1-(4-methoxybenzoyl)-2-tetralone (prepared as in Example 1) in 50 ml. of ether was added dropwise at 0° C. a solution of 0.018 mole of phenylmagnesium bromide in 9 ml. of ether. Upon completion of the addition, the mixture was stirred for twenty minutes. Thin-layer chromatography of the reaction mixture indicated the presence of starting material. An additional 13.5 ml. of the phenylmagnesium bromide solution were added. The mixture was refluxed for 2 hours and then was cooled and poured over iced aqueous ammonium chloride solution. The organic layer was separated and washed with aqueous sodium chloride solution. The mixture then was dried over magnesium sulfate, filtered, and evaporated to give about 5 grams of a yellow oil. In order to obtain more product, a second 5.0 grams of the tetralone was reacted as above. The products were combined, and the total, about 10 grams of oil, was washed with hexane. The portion which was insoluble in the hexane was chromatographed over a 1"×20" neutral $Al_2O_3$ column using, as gradient, a 1:1 mixture of benzene and hexane which progressively diminished in hexane until 100 percent benzene was present. There were obtained 4.67 grams (38 percent) of 3-phenyl-4-(4-methoxybenzoyl)-1,2-dihydronaphthalene. The material was recrystallized from methanol, melting point 106°–107° C.

Analysis, Calcd. for $C_{24}H_{20}O_2$: C, 84.68; H, 5.92; O, 9.40. Found: C, 84.96; H, 6.13; O, 9.65.

Mass spectrum: Theory, 340; Found, 340.

To 2.0 grams (0.006 mole) of the above dihydronaphthalene dissolved in 10 ml. of N,N-dimethyl formamide were added 7.5 mmoles of sodium thioethoxide in 15 ml. of DMF. The addition was carried out under a nitrogen atmosphere and at 80° C. The mixture was maintained at 80° C. for fifteen hours. The mixture then was cooled and poured into an iced aqueous ammonium chloride solution. The resulting mixture was extracted with ethyl acetate, and the ethyl acetate extract was washed four times with aqueous sodium chloride solution. The ethyl acetate then was dried over magnesium sulfate and evaporated to give an oil which was chromatographed rapidly over a 2"×2" silica column using benzene to elute impurities. The product then was eluted with ethyl acetate to give, upon evaporation of the ethyl acetate, 1.69 grams (88%) of 3-phenyl-4-(4-hydroxybenzoyl)-1,2-dihydronaphthalene as a clear pale yellow oil.

Mass spectrum: Theory 326; Found 326.

A mixture of 1.61 grams (4.95 mmoles) of the above product in 10 ml. of dry DMF was added dropwise to 20 ml. of DMF containing 119 mg. (4.95 mmoles) of sodium hydride and freshly distilled 1-chloro-2-pyrrolidinoethane. The addition was made under a nitrogen atmosphere with the temperature being maintained at about 10° C. Upon completion of the resulting effervescence, the mixture was heated at 80° C. for two hours. The mixture then was poured into water, and the total was extracted with ether. The ether extract was washed 5 times with aqueous sodium chloride and dried over magnesium sulfate. The ether layer then was filtered and evaporated to give a grey oil. The oil was chromatographed over a 2"×2" silica column using an ethyl acetate→methanol gradient. There were recovered 1.18 grams (56%) of 3-phenyl-4-[4-(2-pyrrolidinoethoxy)benzoyl]-1,2-dihydronaphthalene.

Mass spectrum: Theory, 423; Found, 423.

The product was converted to the corresponding citrate salt by treatment with 0.59 grams of citric acid in 50 ml. of hot acetone. The resulting mixture was evaporated to dryness, and the residue was stirred for 15 hours with ether to obtain the citrate salt. The salt was vacuum dried to give 1.62 grams (53%) of the title compound, melting point 89°–93° C.

Analysis, Calcd. for $C_{33}H_{37}NO_9 \cdot \frac{1}{2}H_2O$: C, 67.34; H, 6.13; N, 2.25. Found: C, 67.06; H, 6.41; N, 2.66.

EXAMPLE 4

Preparation of the Citrate Salt of 1-[4-(2-Pyrrolidinoethoxy)benzoyl]-2-phenylnaphthalene To 30 ml. of dioxane were added 1.90 grams (5.58 mmoles) of 3-phenyl-4-(4-methoxybenzoyl)-1,2-dihydronaphthalene (prepared as in Example 3) and 2.00 grams (8.81 mmoles) of 2,3-dichloro-5,6-dicyano-1,4-benzoquinone. The resulting mixture was heated at reflux for twelve hours in a nitrogen atmosphere. The mixture then was cooled and evaporated to dryness. Water and ether were added to the residue. The ether layer was separated and washed 5 times with 20 ml. portions of 5 N sodium hydroxide and then with aqueous sodium chloride. The mixture then was dried over magnesium sulfate and evaporated to give 1.9 grams of substantially pure 1-(4-methoxybenzoyl)-2-phenylnaphthalene as a green oil.

Employing substantially the same demethylation procedure as described in Example 3, 1.83 grams (5.41 mmoles) of the above product were treated with sodium thioethoxide to obtain the 1.40 grams (80%) of 1-(4-hydroxybenzoyl)-2-phenylnaphthalene, melting point 204°–205° C.

Analysis, Calcd. for $C_{23}H_{16}O_2$: C, 85.16; H, 4.97; O, 9.86; Found: C, 84.99; H, 5.12; O, 9.58.

To 10 ml. of DMF were added 1.25 grams (3.86 mmoles) of the above product. The resulting mixture was added at about 10° C. to a mixture of 20 ml. of DMF containing 120 mg. (5.0 mmoles) of sodium hydride and 800 mg. of 1-chloro-2-pyrrolidinoethane. Upon completion of the resulting effervescence, the mixture was heated at 80° C. for 3 hours during which time sodium chloride precipitated. The mixture was cooled and evaporated to dryness. The resulting residue was dissolved in a mixture of ethyl acetate and water. The ethyl acetate layer was separated and washed 5 times with 25 ml. each of aqueous sodium chloride solution. The ethyl acetate solution then was dried and evaporated to give 1.62 grams (about 100%) of 1-[4-(2-pyrrolidinoethoxy)benzoyl]-2-phenylnaphthalene as a yellow oil.

The above free base was converted to the corresponding citrate salt in accordance with the method of Example 3 employing 0.811 grams of citric acid hydrate. The title compound was obtained as an amorphous solid which crystallized on standing overnight in ether, melting point 105°–108° C.

Analysis, Calcd. for $C_{33}H_{35}NO_4 \cdot H_2O$: C, 65.55; H, 5.90; N, 2.22; Found: C, 66.90; H, 5.85; N, 2.25.

EXAMPLE 5

Preparation of the Citrate Salt of 3-(4-Methoxyphenyl)-4-[4-(2-pyrrolidinoethoxy)benzoyl]-7-methoxy-1,2-dihydronaphthalene To a solution of about 50 grams (0.24 mole) of p-methoxyphenylmagnesium bromide in tetrahydrofuran (THF) were added at room temperature 30.2 grams (0.08 mole) of 1-(p-benzyloxybenzoyl)-6-methoxy-2-tetralone dissolved in THF. Upon completion of the addition, the entire mixture was warmed to 45° C. Analysis of a sample of the mixture by thin-layer chromatography (TLC) showed the absence of starting material. The mixture then was poured into aqueous ammonium chloride solution, and the resulting mixture was extracted with ethyl acetate. The ethyl acetate extract was washed, dried, and evaporated. The resulting residue was dissolved in benzene, and a catalytic amount of p-toluene- sulfonic acid was added. The mixture was stirred at room temperature until a TLC of the mixture indicated the absence of any carbinol intermediate. The mixture then was washed with water, dried, and concentrated. The residue was chromatographed over one kg. of alumina using 6 l. of benzene. The product was eluted with a mixture of 2 percent ethyl acetate in benzene. The product, 3-(4-methoxyphenyl)-4-(4-benzyloxybenzoyl)-7-methoxy-1,2-dihydronaphthalene was obtained as an oil.

Analysis Calcd. for $C_{32}H_{28}O_4$: C, 80.65; H, 5.92; O, 13.43; Found: C, 80.96, H, 5.91; O, 13.61.

To 150 ml. of N,N-dimethylformamide (DMF) were added 5.4 grams (0.011 mole) of the above dihydronaphthalene. To the mixture were added 30 ml. of DMF containing 0.5 mole of sodium thioethoxide. The resulting mixture was heated under nitrogen at 90° C. Progress of the reaction was followed by TLC. Upon completion, the mixture was poured into an aqueous ammonium chloride solution. The aqueous mixture then was extracted with ethyl acetate. The ethyl acetate extract was separated, washed, dried, and concentrated to an oil. The oil was chromatographed over silica using benzene. Those fractions containing the desired product, 3-(4-methoxyphenyl)-4-(4-hydroxybenzoyl)-7-methoxy-1,2-dihydronaphthalene, were combined and concentrated to dryness to obtain 3.3 grams of a yellow oil. The product was used as is in the next succeeding step.

A mixture of 3.2 grams of the above product in 150 ml. of DMF containing 0.25 grams of sodium hydride was heated in an oil bath at 40° C. for two hours. The mixture became reddish in appearance. Upon completion of the heating, the mixture was cooled to room temperature, 1.2 grams of 1-chloro-2-pyrrolidinoethane were added, and the mixture was heated to 60°–70° C. for about one hour. The resulting mixture then was stirred at room temperature overnight after which it was poured into a large amount of water, and the aqueous mixture was extracted with ethyl acetate. The ethyl acetate extract was washed several times with water and sodium bicarbonate solution. The ethyl acetate mixture then was dried over magnesium sulfate and was concentrated to dryness to obtain 3.2 grams of a pale yellow oil. The oil was purified by chromatography over silica using ethyl acetate to obtain 3.0 grams of 3-(4-methoxyphenyl)-4-[4-(2-pyrrolidinoethoxy)benzoyl]-7-methoxy-1,2-dihydronaphthalene. The above free base product (2.9 grams) was dissolved in 150 ml. of acetone, and one equivalent of citric acid dissolved in hot acetone was added. The mixture was maintained at 0° C. for about three days. The product failed to crystallize. The mixture was evaporated, and the residue was dissolved in a minimum of acetone. Ethyl ether (500 ml.) was added, and the resulting mixture was stirred overnight. The product crystallized and was collected by filtration and vacuum dried to obtain 3.2 grams of the title compound.

Analysis Calcd. for $C_{37}H_{41}NO_{11}$: C, 65.77; H, 6.12; N, 2.07; Found: C, 65.54; H, 6.10; N, 2.28.

EXAMPLE 6

Preparation of the Citrate Salt of 3-(4-Methoxyphenyl)-4-[4-(2-piperidinoethoxy)benzonyl]-1,2-dihydronaphthalene To a suspension of 0.269 grams (0.011 mole) of sodium hydride washed free of mineral oil and 1.82 grams (0.012 mole) of 1-chloro-2-piperidinoethane in 50 ml. of DMF at 0° C. and under nitrogen were added 4.0 grams (0.01 mole) of a solution of 3-(4-methoxyphenyl)-4-(4-hydroxybenzoyl)-1,2-dihydronaphthalene (prepared as in Example 1) in 20 ml. of DMF. The solution was added dropwise with stirring. When effervescence had for the most part ceased, the mixture was heated at 50° C. for several hours. Examination of a sample of the mixture by TLC indicated that only a small amount of the starting material remained. The DMF was evaporated, and the concentrated mixture was poured over ice water and ethyl acetate. The ethyl acetate was separated and was washed with aqueous sodium chloride, dried over potassium carbonate, filtered, and evaporated. The resulting oil was chromatographed over a 1.5"×12" silica column using the following as a double gradient:

(1) 10 percent ethyl acetate in benzene (500 ml.)→20 percent ethyl acetate in benzene (2 liters).

(2) 20 percent ethyl acetate in benzene (1.5 liters)→1:1 mixture of methanol and ethyl acetate (1.5 liters).

The appropriate fractions were concentrated to give an almost colorless oil. The oil was dissolved in ethyl acetate, and the ethyl acetate solution was dried over potassium carbonate, filtered, and evaporated to give 4.7 grams (91 percent) of the free base of the title compound as a pale yellow oil.

The free base (3.4 grams; 7.28 mmoles) was treated with 1.49 grams (7.1 mmoles) of citric acid monohydrate in about 20 ml. of boiling acetone. When a clear solution was obtained, the acetone was evaporated, 300 ml. of anhydrous ether were added, and the resulting precipitate was stirred magnetically overnight. The title compound (5.2 grams) was collected as a white powder.

Analysis, Calculated for $C_{37}H_{41}NO_{10}$: C, 67.36; H, 6.26; N, 2.12; O, 24.25. Found: C, 67.25; H, 5.96; N, 1.84; O, 24.18.

EXAMPLE 7

Preparation of the Citrate Salt of 3-(4-Methoxyphenyl)-4-[4-(2-dimethylaminoethoxy)-benzoyl]-1,2-dihydronaphthalene To 50 ml. of acetone were added 4.0 grams (0.0112 mole) of 3-(4-methoxyphenyl)-4-(4-hydroxybenzoyl)-1,2-dihydronaphthalene (prepared as in Example 1), 1.81 grams (0.0168 mole) of 1-chloro-2-dimethylaminoethane (freshly prepared from the hydrochloride), and 2.32 grams (0.0168 mole) of finely powdered potassium chloride. The resulting mixture was refluxed under nitrogen with stirring for 72 hours after which time examination of a sample of the mixture by TLC indicated that the starting material was gone. The reaction mixture then was poured over ice, and the resulting mixture was extracted with ether. The ether was washed three times with saturated aqueous sodium chloride, dried over potassium carbonate, filtered, and evaporated to obtain 4.51 grams (94 percent) of the free base of the title compound as a brown oil. The oil was vacuum dried and then was converted to the citrate salt by treatment with 2.17 grams (0.0104 mole) of citric acid monohydrate in 50 ml. of hot acetone. Evaporation of the acetone and stirring of the residue with ether gave 5.2 g. (89%) of the title compound as an amorphous solid.

Analysis, Calculated for $C_{34}H_{37}NO_{10}$: C, 65.90; H, 6.02; N, 2.26; O, 25.84. Found: C, 66.17; H, 6.23; N, 2.37; O, 26.06.

EXAMPLE 8

Preparation of the Mesylate Salt of 3-(4-Hydroxy-phenyl)-4-[4-(2-pyrrolidinoethoxy)benzoyl]-1,2-dihydronaphthalene To 25 ml. of methyl ethyl ketone were added 1.0 grams (2.92 mmole) of 3-(4-hydroxyphenyl)-4-(4-hydroxybenzoyl)-1,2-dihydronaphthalene, 0.497 g. (2.92 mmole) of 1-chloro-2-pyrrolidinoethane hydrochloride, and 1.21 g. (8.77 mmole) of finely powdered potassium carbonate. The resulting mixture was refluxed for 16 hours. The mixture then was cooled and poured into a mixture of water and ethyl acetate. The resulting mixture was rendered acidic by addition of 1 N hydrochloric acid and then alkaline by addition of sodium bicarbonate. The organic layer was separated, washed with aqueous sodium chloride, dried over magnesium sulfate, and evaporated to give a yellow oil. The resulting oil was chromatographed over a 2"×2" silica column. Ethyl acetate was employed to elute about 0.5 g. of unreacted starting material, and methanol was empolyed to elute about 0.4 g. of the free base of the title compound as a yellow oil. The free base (362 mg.; 0.825 mmole) was converted to the mesylate salt by treatment with an equivalent of methanesulfonic acid in acetone. The title compound was obtained as an amorphous solid.

Analysis, Calculated for $C_{31}H_{35}NO_6S$: C, 67.27; H, 6.21; N, 2.61. Found: C, 67.25; H, 6.19; N, 2.69.

EXAMPLE 9

Preparation of the Mesylate Salt of 3-(4-Methoxyphenyl)-4-[4-(2-hexamethyleneiminoethoxy)benzoyl]-1,2-dihydronaphthalene To 50 ml. of methyl ethyl ketone were added 3.0 g. (8.43 mmole) of 3-(4-methoxyphenyl)-4-(4-hydroxybenzyl)-1,2-dihydronaphthalene, 1.84 g. (9.27 mmole) of 1-chloro-2-hexamethyleneiminoethane hydrochloride, and 3.5 g. (25.3 mmole) of finely powdered potassium carbonate. The mixture was refluxed for 48 hours. The mixture then was poured into water, and ethyl acetate was added. The resulting organic layer was separated, washed with aqueous sodium chloride, dried, and evaporated to a yellow oil. The oil was chromatographed over a 2"×4" silica column using, as gradient, benzene→10% ethyl acetate and benzene→1:1 methanol and ethyl acetate. The free base of the title compound was recovered (2.15 g.; 55%) as a pale yellow oil. The oil (2.09 g.; 4.48 mmole) was treated with 0.431 g. (4.48 mmole) of methanesulfonic acid in 10 ml. of acetone. Upon scratching and cooling of the mixture, crystals formed. The mixture was cooled overnight, and 1.97 g. (42%) of the title compound were obtained as white crystals, m.p. 123°–125° C.

Analysis, Calculated for $C_{34}H_{41}NO_6S$: C, 68.61; H, 6.80; N, 2.42; O, 16.62; S, 5.55. Found: C, 68.38; H, 6.62; N, 2.40; O, 16.70; S, 5.55.

EXAMPLE 10

Preparation of the Mesylate Salt of 3-(4-Methoxyphenyl)-4-[4-(2-piperidinoethoxy)benzoyl]-1,2-dihydronaphthalene To 150 ml. of methyl ethyl ketone were added 7.8 g. (21.9 mmole) of 3-(4-methoxyphenyl)-4-(4-hydroxybenzoyl)-1,2-dihydronaphthalene, 4.84 grams (23.6 mmole) 1-chloro-2-piperidinoethane hydrochloride, and 14.5 g. (109 mmole) of potassium carbonate. The resulting mixture was refluxed overnight. The mixture then was poured into a mixture of water and ethyl acetate. The resulting organic layer was separated, washed with aqueous sodium chloride, dried over magnesium sulfate, and evaporated in vacuo to obtain the free base of the title compound as a yellow oil. The oil was dissolved in 30 ml. of acetone and was treated with 2.105 g. (21.9 mmole) of methanesulfonic acid. The mixture was cooled and scratched, and the title compound was collected at −40° C. and washed well with acetone and ether cooled to about −60° C. The solid then was vacuum dried at 100° C. to obtain 11.21 g. (91%) of the title compound as a white crystalline solid, m.p. 157°–158° C.

Analysis, Calculated for $C_{33}H_{39}NO_6S$: C, 68.18; H, 6.62; N, 2.48; O, 17.03; S, 5.69. Found: C, 68.11; H, 6.76; N, 2.50; O, 16.94; S, 5.43.

EXAMPLE 11

Preparation of the Mesylate Salt of 3-(4-Methoxyphenyl)-4-(4-diethylaminoethoxybenzoyl)-1,2-dihydronaphthalene To 75 ml. of methyl ethyl ketone were added 4.0 g. (11.2 mmole) of 3-(4-methoxyphenyl)-4-(4-hydroxybenzoyl)-1,2-dihydronaphthalene, 2.41 g. (14 mmole) of 1-chloro-2-diethylaminoethane hydrochloride, and 7.93 g. (56 mmole) of finely powdered potassium carbonate. The mixture was refluxed overnight, and, employing the method of Example 10, 5.67 g. of the free base of the title compound were obtained as a yellow oily material. The oil was treated with 1.07 g. (11.2 mmole) of methanesulfonic acid in about 15 ml. of acetone. The resulting mixture was maintained with cooling for several days after which white crystals appeared. The crystals were somewhat hygroscopic and were collected as quickly as possible and vacuum dried. There were obtained 4.3 g. (70%) of the title compound as a white crystalline solid, m.p. 80°–90° C. (gradual effervescence). The product indicated the presence of some acetone; it therefore was vacuum dried at 70° C. overnight.

Analysis, Calculated for $C_{31}H_{39}NO_6S$: C, 67.24; H, 7.10; N, 2.53; O, 17.34. Found: C, 67.48; H, 6.92; N, 2.43; O, 17.57.

EXAMPLE 12

Preparation of the Mesylate Salt of 3-(4-Methoxyphenyl)-4-(4-diisopropylaminomethoxybenzoyl)-1,2-dihydronaphthalene To 75 ml. of methyl ethyl ketone were added 3.84 g. (10.8 mmole) of 3-(4-methoxyphenyl)-4-(4-hydroxybenzoyl)-1,2-dihydronaphthalene, 2.70 g. (13.5 mmole) of 1-chloro-2-diisopropylaminoethane hydrochloride, and 7.11 g. (54 mmole) of finely powdered potassium carbonate. The mixture was allowed to reflux overnight, and, upon workup in accordance with the procedure of Example 10, 5.64 g. of the free base of the title compound were obtained as a yellow oily substance. The oily product was treated with 1.04 g. (10.8 mmole) of methanesulfonic acid in about 25 ml. of acetone. The mixture was cooled, and crystals slowly appeared. The crystals were collected at −40° C. with the aid of acetone cooled to −60° C. Vacuum drying of the product gave 5.1 g. (82%) of the title compound, m.p. 175°–176° C.

Analysis, Calculated for $C_{33}H_{41}NO_6S$: C, 68.37; H, 7.31; N, 2.42; O, 16.56; S, 5.53. Found: C, 68.08; H, 6.91; N, 2.21; O, 16.72; S, 5.60.

The compounds of this invention are tested for antifertility activity both pre- and postcoitally.

In the precoital antifertility test, fifty young adult virgin female rats weighing 200–230 g. each are separated into ten groups of five each. One of the groups serves as the control group and the other nine groups as experimental groups, each such experimental group receiving test compound at a particular dose level. The test compound for each group of five rats is prepared in corn oil such that the daily administration is in 0.1 ml. of vehicle. The designated quantity of the test compound in the vehicle is administered to each rat within the defined group subcutaneously (sc) daily. The control group receives only the vehicle. Administration of the vehicle or the combination of test compound and vehicle is continued on a daily basis for 15 days. On the 5th day of treatment, two adult male rats weighing at least 250 g. each are added to each group, and cohabitation is continued until the 15th day at which time the male rats are withdrawn from the group. Each group of female rats then is maintained for an additional seven days after which the rats are sacrificed and examined for the presence of viable or resorbing fetuses.

The number of animals that exhibit evidence of pregnancy over the number of animals in the group is the pregnancy ratio. A compound is considered active when the ratio is 0/5 or 1/5. A ratio of 2/5 constitutes marginal activity, and anything higher is inactive.

In the postcoital test, adult cyclic virgin female rats weighing at least 200 grams are used as test subjects. The females are placed with a male in single cages and are examined daily for vaginal plugs or for sperm in the vagina. When evidence of breeding is present, the male is removed and daily administration of the test compound is begun and is continued for 11 days. On the 12th day, the female is sacrificed and is examined for the presence of viable and/or resorbing fetuses.

The pregnancy ratio (number of animals pregnant per number of animals in the group) is given. Since all test animals represent confirmed breedings, the figures for control animals are quite high. Therefore, a 50 percent pregnancy rate is deemed to indicate acitivity.

In addition, the total number of viable fetuses and the total number of resorption sites are given as an indication of fecundity and of rate of implantation. Since, in the control, the customary number of viable fetuses per animal is about 11 or 12, any reduction of this figure is also an indicator of activity.

The Table I following illustrates the antifertility activity of compounds of this invention.

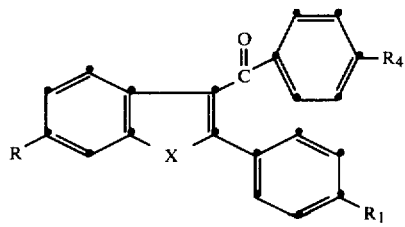

TABLE I
Antifertility Activity

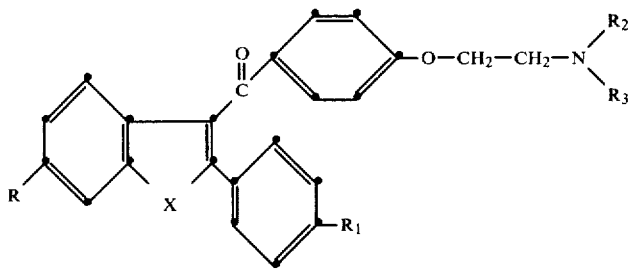

| | Compound | | | | Precoital | Postcoital | | |
|---|---|---|---|---|---|---|---|---|
| | | $-N\begin{matrix}R_2\\R_3\end{matrix}$ | | Dose | Pregnancy Ratio | Ratio No. Pregnant/ | No. | No. |
| R | $R_1$ | | X | mg./day | P/5 P = | No. in Group | Viable | Resorptions |
| H | $-OCH_3$ | pyrrolidino[a] | $-CH_2-CH_2-$ | 0.5 | — | 0/2 | 0 | 0 |
| | | | | 0.05 | 0 | 0/5 | 0 | 0 |
| | | | | 0.01 | 1 | 1/5 | 0 | 1 |
| | | | | 0.005 | — | 2/5 | 14 | 0 |
| | | | | 0.001 | 5 | — | — | — |
| $-OCH_3$ | H | pyrrolidino[a] | $-CH_2-CH_2-$ | 0.05 | 0 | 0/3 | 0 | 0 |
| | | | | 0.01 | 2 | 4/6 | 44 | 0 |
| | | | | 0.005 | — | 5/5 | 44 | 3 |
| | | | | 0.001 | — | 3/3 | 35 | 0 |
| H | H | pyrrolidino[a] | $-CH_2-CH_2-$ | 0.05 | — | 0/3 | 0 | 0 |
| | | | | 0.01 | — | 1/6 | 2 | 0 |
| | | | | 0.005 | — | 2/4 | 12 | 7 |
| H | H | pyrrolidino | $-CH=CH-$ | 0.1 | — | 1/2 | 7 | 0 |
| | | | | 0.01 | — | 2/3 | 21 | 0 |
| | | | | 0.05 | — | 3/3 | 32 | 0 |
| $-OCH_3$ | $-OCH_3$ | pyrrolidino[a] | $-CH_2-CH_2-$ | 0.05 | — | 0/3 | 0 | 0 |
| | | | | 0.01 | — | 1/3 | 2 | 0 |
| | | | | 0.005 | — | 2/3 | 13 | 3 |

[a]Citrate Salt

We claim:

1. A compound of the formula in which X is $-CH_2-CH_2-$ or $-CH=CH-$; R is hydrogen, hydroxyl, or $C_1-C_5$ alkoxy; $R_1$ is hydrogen, hydroxyl, or $C_1-C_5$ alkoxy; and $R_4$ is hydroxyl.

2. Compound of claim 1, in which X is $-CH_2-CH_2-$.

3. Compound of claim 1, in which X is $-CH=CH-$.

* * * * *